United States Patent [19]

Pruitt

[11] Patent Number: 4,596,579
[45] Date of Patent: Jun. 24, 1986

[54] VOICE PROSTHESIS WITH TRACHEAL GUARD

[76] Inventor: Robert L. Pruitt, 314 Leland St., Peoria, Ill. 61605

[21] Appl. No.: 597,729

[22] Filed: Apr. 6, 1984

[51] Int. Cl.⁴ .............................................. A61F 2/20
[52] U.S. Cl. ...................................................... 623/9
[58] Field of Search .................... 128/207.16, 200.26; 3/1.3

[56] References Cited

U.S. PATENT DOCUMENTS

| | | | |
|---|---|---|---|
| 3,088,466 | 5/1963 | Nichols | 128/351 |
| 3,225,767 | 12/1965 | Smith | 128/351 |
| 3,688,774 | 9/1972 | Akiyama | 128/351 |
| 4,269,184 | 5/1981 | Montgomery | 128/207.14 |
| 4,304,228 | 12/1981 | Depel | 128/200.26 |
| 4,315,505 | 2/1982 | Crandall et al. | 128/200.26 |
| 4,325,366 | 4/1982 | Tabor | 128/207.16 |
| 4,435,853 | 3/1984 | Blom et al. | 3/1.3 |

*Primary Examiner*—Richard J. Apley
*Assistant Examiner*—James Prizant
*Attorney, Agent, or Firm*—McCaleb, Lucas & Brugman

[57] ABSTRACT

A voice prosthesis formed as a small diametered, flexible walled, generally linear tube having an air valve at its inner end, a flexible retention collar intermediate its ends and a mounting tab at its outer end is adapted for insertion into a surgically placed tracheoespohageal fistula following laryngectomy for restoring the power of speech to the user. A larger diametered, relatively short, curved tracheal tube or cannula provided with a retention collar at its outer end is insertable into the tracheal stoma to prevent closure thereof; the cannula partially surrounding and guarding the mounted prosthesis which transects the tracheal cannula, by passing through an elongated channel opening, which is open at one end and extends along the outer wall of the tracheal tube. The arrangement of the two tubes is such that the larger tracheal cannula is readily inserted and withdrawn from the tracheal stoma without disturbing the mounted voice prosthesis.

5 Claims, 5 Drawing Figures

VOICE PROSTHESIS WITH TRACHEAL GUARD

This invention relates to surgical appliances and more particularly to tracheotomy tubes and improvements therein whereby the same may be used with a mounted tracheoesophageal voice prosthesis.

For various reasons certain persons suffer respiratory malfunction caused by known throat or nasal defects and blockages. Under such circumstances it is common practice for surgeons to provide an incision near the base of the afflicted patient's throat to establish communication between the atmosphere and the patient's trachea or windpipe. This incision is commonly referred to as a tracheal stoma. A curved tube known as a tracheotomy tube or cannula is then normally inserted into the trachea through this stoma to facilitate free passage of air, permitting the patient to breathe. In certain instances, due to disease such as cancer, it is necessary to remove the patient's larnyx whereupon the power of speech is lost. In such instances it is common to provide a tracheal incision or stoma for reception of a tracheotomy tube or cannula to which an artificial larnyx may be connected enabling the afflicted person to speak. In other instances a voice prosthesis comprising a small diametered generally linear tubular member is provided to extend through the tracheal stoma across the trachea and into a esophageal fistula. This device enables the user to expel air into his esophageal passageway. Speech is restored to the user by blocking off air flow through the stoma and then forcing air flow upwardly through the prothesis into the esophageal passageway and across the soft tissue of the pharyngeal-esophageal segment.

In utilizing such an esophageal mounted voice prosthesis, it is of paramount importance that the fistula or opening through the esophageal wall be prevented from closing over. This is usually accomplished by maintaining the prosthesis in its inserted position at all times except for short periods when the same must be removed for cleaning purposes at which time a dummy prosthesis is normally inserted to maintain the integrity of the esophageal opening. Of like importance is the ability to maintain the opening or stoma into the trachea through which the voice prosthesis is inserted. Under current practice this is accomplished generally by periodically inserting a normal tracheotomy tube in the tracheal opening, in which case the voice prosthesis must be removed, accompanied by a loss in speaking ability. If no tracheal tube is used then the patient must hazard the risk of the gradual closing over of the tracheal stoma which requires eventual surgical repair and reopening in order to provide a passage for the voice prosthesis.

The present invention is directed to an improved tracheal cannula for use with a tracheoesophageal voice prosthesis. In brief this is accomplished by providing an elongated channel opening in one wall of a short curvelinear tracheotomy tube whereby a generally linear tubular voice prosthesis may be mounted in the esophageal fistula to extend along an axis that transects the mounted tracheotomy tube. The virtue of this arrangement is that the tracheotomy tube may be freely inserted and withdrawn from the tracheal stoma without disturbing the esophagael mounted voice prosthesis. This permits cleansing of the tracheotomy tube and prevents closing over of the trachael stoma.

It is a principle object of this invention to provide a combined voice prosthesis and tracheal tube for maintaining the prosthesis mounted in a tracheoesophageal fistula while permitting insertion and removal of the tracheal tube thereover.

It is another important object of this invention to provide a voice prosthesis of the type mounted in an esophageal fistula and a cooperating tracheotomy tube partially surrounding the voice prosthesis where it passes through a tracheal stoma.

Still another important object of this invention is to provide a new, improved and simplified combination of a tracheoesophageal voice prosthesis and cooperating tracheotomy tube arranged so that the tracheotomy tube may be readily mounted in and withdrawn from the tracheal stoma without disturbing the esophageal mounted prosthesis.

Having described this invention, the above and further objects features and advantages thereof will appear to those of skill in this art from the following detailed description of a preferred embodiment, illustrated in the accompanying drawings and representing the best mode presently contemplated for enabling those with skill in this art to make and practice this invention.

Figure 1:
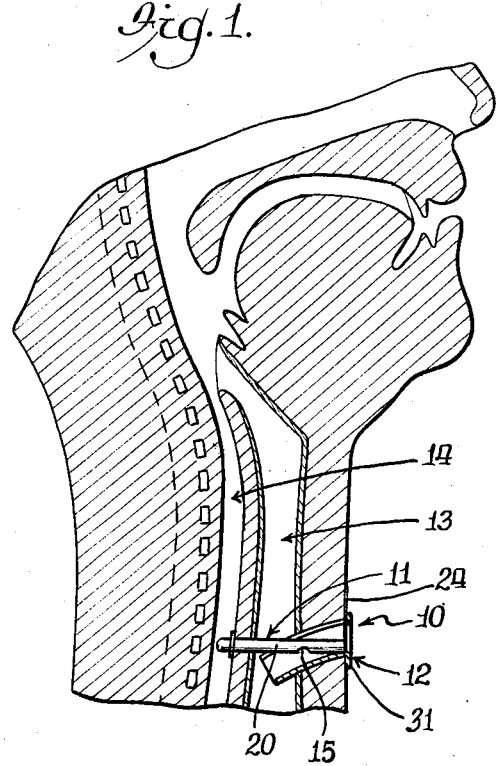
FIG. 1 is a schematic cross-sectional view of a human throat area showing the mounted position of the voice prosthesis and tracheal guard of this invention.

Turning now to the details of the preferred embodiment of this invention illustrated in the accompanying drawings, initial reference is made to FIG. 1, which schematically illustrates the human's throat area with the improved assembly 10 according to this invention mounted in operating position.

As indicated, assembly 10 comprises a tubular tracheoesophageal voice prosthesis 11 and a short trachea guard or cannula 12 mounted in the throat so that the prosthesis 11 extends across the tracheal passageway 13 and into the esophageal passageway 14. The tracheal cannula 12, on the other hand is disposed in surrounding relation to a portion of prosthesis 11 and extends only into in the tracheal passageway 13. So mounted the trachea cannula 12 permits free entry of air into the tracheal passageway and the prosthesis 11 likewise provides for the entry of air into the esophageal passageway when the stoma is occluded. Speaking is accomplished by closing off the open outer end of the stoma as by pressing one's thumb thereover whereby air may be forced upwardly through the prothesis and into the esophagus in a known manner.

Considering the particulars of the prosthesis 11, the preferred form illustrated comprises an elongated hollow tubular body 20 having a window 15 intermediate it's ends a one way valve 21 comprising a slit through body 20 near the closed inner end 22 thereof. An enlarged flexible retention collar portion 23 is provided adjacent valve means 21 for purposes of locking the prosthesis in the esophageal fistula, as will be described in greater detail presently. The outer end of the body 20 is equipped with an intergrally formed mounting tab 24 comprising a flexible, generally rectangular shaped flat strip, of the same material as the body 20. Tab 24 operationally resides on the exterior of the user's throat where it is affixed by suitable glue, adhesive tape or the like. A voice prosthesis of this order is of known structure and is readily available commercially from the American Hospital Supply Corporation of Chicago, Ill. or Bivona Surgical of Hamond, Ind. Typically prosthesis 11 is constructed of silicone rubber or some equivalent soft pliable material to provide a flexible device which is non-irritating to the user and is particularly capable is being inserted through the trachea and esophageal fistula without damage to such surgically placed openings.

Figure 3:
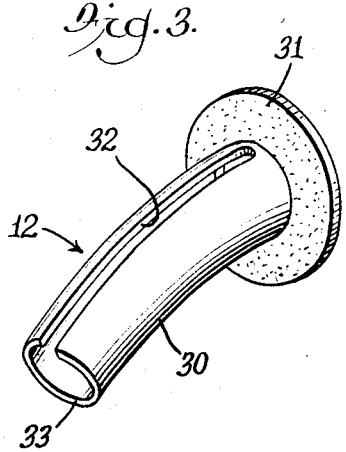
FIG. 3 is a perspective view of the tracheal guard seen in FIG. 1.
Figure 2:
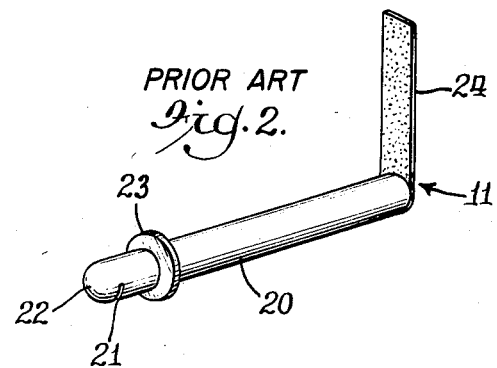
FIG. 2 is a perspective view of the prior art voice prosthesis shown in FIG. 1.

With reference to FIG. 3 of the drawings, the features and details of the improved tracheal guard or cannula 12 are shown as comprising a relatively short tubular main body portion 30 having an enlarged annular retention flange 31 at the outer end thereof. Body 30 may be straight but preferably is curvelinear, of cylindrical cross-section and has an elongated channel opening 32 formed along the upperside of the body portion 30. Channel 32 is open at its inner end for reception and passage of the prosthesis 11.

In practice the cannula or trachea tube 12 is formed of semi-rigid material, such as nylon or a similar plastic capable of withstanding sterilizing temperatures, with the body portion 30 thereof intergrally formed with retention collar 31 as by a molding operation. The tubular body 30 of the cannula 12 is of course much larger in diameter than that of the prosthesis tubular body 20 (roughly twice the diameter) so that prosthesis 11 may pass through the interior of body portion 30 while permitting air to enter the trachea passageway 13 via the clearance space therebetween. The operationally innermost end 33 of the cannula 12 preferably is rounded over to avoid sharp edges for the comfort of the user, particularly when inserting the same into the tracheal stoma 40, as shown in FIG. 4.

Figure 4:
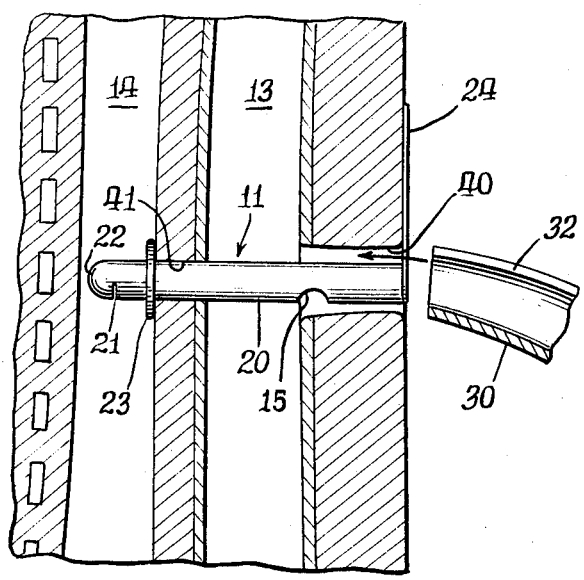
FIG. 4 is an enlarged schematic cross-sectional view of the human throat area showing the voice prosthesis mounted in the tracheoesophageal fistula and illustrating the manner of inserting the tracheal guard thereover.
Figure 5:
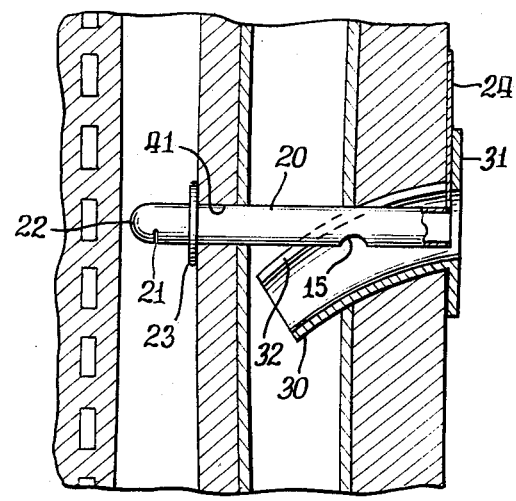
FIG. 5 is an enlarged cross-sectional view similar to FIG. 4, showing the mounted position of the voice prosthesis and tracheal guard.

Having described the details and features of the prosthesis 11 and trachea cannula 12, the use and operation thereof will best be understood with reference to FIGS. 4 and 5 of the drawings.

As set out in FIG. 4, the voice prosthesis 11 is adapted to be inserted through the large tracheal stoma 40 and into the smaller esophageal fistula 41 with the retention collar portion 23 thereof passing through the esophageal wall into the passageway 14 with the valve means 21 thereof located in a downward position. The mounting tab 24 is disposed to extend upwardly along the exterior of the user's neck to which the same is affixed as by adhesive or tape. In mounting the prosthesis 11 it is normal to move the closed inner end thereof through the esophageal fistula until the collar 23 is felt to snap open within the esophagus 14. Thereafter the prosthesis is pulled or gently withdrawn until the collar 23 is seated against the wall of the esophagus, in the manner illustrated in FIG. 4. An insertion tool comprising an elongated rodlike member is available for assisting in the mounting of the prosthesis in its operational position as above described. The primary functions of the prosthesis are to prevent the esophageal fistula 41 from closing and to permit the flow of air via window 15 into the esophagus for purposes of voice reproduction in a known manner. The one way valve means 21 thereof permits the flow of air into the esophagus while eliminating backflow or reflux therethrough during coughing, swallowing and like movements. The prosthesis normally may be maintained in its mounted position as illustrated in FIG. 4 for days or weeks at a time without requiring daily removal although it is recommended that the same be removed for occasional cleaning or if it ceases to function properly, as from a damaged valve or the like.

As noted previously one of the major difficulties encountered in using a voice prosthesis of the order herein illustrated and described is the tendency of the tracheal stoma 40 to close over even after a short period of time. In that event, current practice requires the stoma 40 to be reopened by surgical procedures. In other instances a normal tracheal tube periodically is inserted through stoma 40 (after removal of the prosthesis) in an effort to maintain the stoma in open condition.

According to this invention, the improved tracheal cannula 12 is capable of being moved through the tracheal stoma 40 into the tracheal passageway 13 and removed therefrom while the prosthesis 11 remains in its mounted position as illustrated in FIG. 4. This desirable function is accomplished by virtue of the elongated open ended channel or opening 32 formed in and along one wall of the cannula 12 as shown in FIG. 3. As indicated in FIG. 4, by virtue of the open inner end and extent of the channel opening 32, the mounting tab 24 of the mounted prosthesis as well as the tubular body 20 thereof is adapted to pass in and along opening 32 as the body 30 is inserted into the tracheal stoma 40 or withdrawn therefrom. Thus, by aligning the open end of opening 32 with the mounting tab 24 the prosthesis acts to guide cannula 12 into the stoma 40 and tracheal passageway 13, eventually being positioned as illustrated in FIG. 5. It will be noted that the linear prosthesis transects the curvelinear body of the mounted tracheal cannula 12, in the assembled positioning of members 11 and 12.

When mounted, the outer retention flange 31 of the tracheal cannula is disposed exteriorly over the prosthesis mounting tab 24 thereby assisting in the retention of the prosthesis in its operating position and preventing the tracheal cannula from accidentally moving or dropping into the trachea, which could be of fatal consequence. Normally once the tracheal tube 12 is mounted as illustrated in FIG. 5, adhesive tape is applied over flange portion 31 thereof to fasten the same to the user's neck thereby retaining the same in operating position until its removal is desired.

With the above described arrangement the tracheal cannula 12 guards the prosthesis 11, maintains the tracheal stoma 40 in open condition and may be readily inserted and removed from stoma 40 as required; usually being positioned therein during the active hours of the user or patient and removed for sleeping purposes or in other situations where presence of the tracheal cannula would cause unusual discomfort.

From the foregoing is believed those of skill in this art will readily recognize the novel advancement of the voice prosthesis and tracheal guard combination of this invention over the prior art and will appreciate that while the same has been described in conjunction with a particular preferred embodiment the same is obviously susceptible to variation and substitution of materials and equivalents without departing from the spirit and scope of this invention which is intended to be unlimited by the foregoing except as may appear in the following appended claims.

Embodiments of the invention in which an exclusive property or privilege is claimed are defined as follows:

1. In combination, a tubular tracheoesophageal human voice prosthesis, and a tracheal cannula having an open ended tubular body formed with a channel opening in one wall thereof receptive of said prosthesis for passage therethrough of said voice prosthesis whereby the tracheal cannula may be inserted and withdrawn from a tracheal stoma without disturbing the tracheoesophageal mounted position of the prosthesis.

2. The combination of claim 1 wherein said opening is elongated, open at one end and dimensioned to clear said prosthesis throughout its length whereby said cannula passes over the mounted prosthesis when inserted or removed from the tracheal stoma.

3. The combination of claim 2 in which the prosthesis is provided with a mounting tab at its outer end attachable to the user's neck to extend partially over said stoma, and said channel opening extends substantially along the length of said body and is receptive of said tab via said open end thereof.

4. The combination of claim 1, wherein said prosthesis is a flexible walled, generally linear tubular member, and said tracheal cannula, when mounted in said stoma, transects the linear axis of said prosthesis and is sufficiently rigid to guard the same and prevent closure of said stoma.

5. The combination of claim 1, and an enlarged retention collar surrounding an outer open end of said trachael cannula to operatively limit insertion of said cannula into the tracheal passageway.

* * * * *